United States Patent
Chang et al.

(10) Patent No.: US 8,673,626 B2
(45) Date of Patent: Mar. 18, 2014

(54) BIOSENSOR FOR ANALYZING QUANTITATIVELY ANALYTE WITH A PREDETERMINED SIZE AND LARGER THAN, AND MANUFACTURING METHOD THEREOF

(75) Inventors: Je-Young Chang, Anyang-si (KR); Seung-Joo Kang, Seoul (KR)

(73) Assignee: All Medicus Co., Ltd., Anyang-si (KR)

( * ) Notice: Subject to any disclaimer, the term of this patent is extended or adjusted under 35 U.S.C. 154(b) by 1060 days.

(21) Appl. No.: 12/069,273

(22) Filed: Feb. 7, 2008

(65) Prior Publication Data

US 2008/0311648 A1    Dec. 18, 2008

Related U.S. Application Data

(62) Division of application No. 10/558,222, filed as application No. PCT/KR2004/001197 on May 21, 2004, now Pat. No. 7,332,314.

(30) Foreign Application Priority Data

May 23, 2003   (KR) .................. 10-2003-0033068

(51) Int. Cl.
    *C12M 1/34*         (2006.01)
(52) U.S. Cl.
    USPC ............. 435/287.2; 204/403.01; 204/403.03; 422/82.01; 436/524; 436/525; 436/806; 436/809
(58) Field of Classification Search
    None
    See application file for complete search history.

(56) References Cited

U.S. PATENT DOCUMENTS

| | | |
|---|---|---|
| 4,964,972 A | 10/1990 | Sagiv et al. |
| 5,620,850 A | 4/1997 | Bamdad et al. |
| 5,652,059 A | 7/1997 | Margel |
| 5,686,549 A | 11/1997 | Grainger et al. |
| 5,725,788 A | 3/1998 | Maracas et al. |
| 5,827,417 A | 10/1998 | Porter et al. |
| 5,919,576 A * | 7/1999 | Hui et al. ............... 428/545 |
| 5,922,214 A | 7/1999 | Liu et al. |
| 6,001,587 A | 12/1999 | Turner et al. |
| 6,031,756 A | 2/2000 | Gimzewski et al. |
| 6,096,497 A | 8/2000 | Bauer |

(Continued)

FOREIGN PATENT DOCUMENTS

| | | |
|---|---|---|
| KR | 2003-45490 A | 6/2003 |
| KR | 2004-17697 A | 2/2004 |

OTHER PUBLICATIONS

Sengwa et al., Dielectric properties of low molecular weight poly-(ethylene glycol)s, 2000, Polym In,, 49: pp. 559-608.*

(Continued)

*Primary Examiner* — Chris L Chin
(74) *Attorney, Agent, or Firm* — Haynes and Boone LLP

(57) ABSTRACT

The present invention discloses a biosensor for quantitatively analyzing a bio-material and a manufacturing method thereof. The biosensor has an exposed conductive region of a few-nanometer scale distributed on an insulated metallic substrate in a desired pattern or randomly. The quantitative analysis of protein can be carried out by means of simplified procedures, without the necessity of rinsing out a signal-producing material, which is non-specifically bonded to the materials to be analyzed. The biosensor utilizes only the size of the molecules, and thus can be universally used for the analysis of bio-materials. A selective and separate analysis can be realized in which interference caused by other materials is significantly reduced.

13 Claims, 6 Drawing Sheets

(56) References Cited

U.S. PATENT DOCUMENTS

| | | |
|---|---|---|
| 6,114,099 A | 9/2000 | Liu et al. |
| 6,127,127 A | 10/2000 | Eckhardt et al. |
| 6,156,393 A | 12/2000 | Polanyi et al. |
| 6,183,815 B1 | 2/2001 | Enick et al. |
| 6,241,863 B1 | 6/2001 | Monbouquette |
| 6,270,946 B1 | 8/2001 | Miller |
| 6,287,874 B1 | 9/2001 | Hefti |
| 6,312,809 B1 | 11/2001 | Crooks et al. |
| 6,322,963 B1 | 11/2001 | Bauer |
| 6,322,979 B1 | 11/2001 | Bamdad et al. |
| 6,346,387 B1 | 2/2002 | Stewart et al. |
| 6,432,723 B1 | 8/2002 | Plaxco et al. |
| 6,436,699 B1 | 8/2002 | Berggren et al. |
| 6,444,318 B1 | 9/2002 | Guire et al. |
| 6,444,321 B1 | 9/2002 | Arnebrant et al. |
| 6,492,096 B1 | 12/2002 | Liu et al. |
| 6,503,701 B1 | 1/2003 | Bauer |
| 2001/0021534 A1* | 9/2001 | Wohlstadter et al. .......... 436/518 |
| 2002/0006626 A1* | 1/2002 | Kim et al. ...................... 435/7.1 |
| 2002/0106702 A1* | 8/2002 | Wagner et al. ................. 435/7.9 |
| 2003/0054333 A1 | 3/2003 | Hickman et al. |

OTHER PUBLICATIONS

Korean Patent Abstracts, Publication No. 1020030045490, Jun. 11, 2003, 2 pp.

Korean Patent Abstracts, Publication No. 1020040017697, Feb. 27, 2004, 2 pp.

International Search Report of PCT/KR2004/001197 dated Oct. 5, 2004, 3 pages.

International Preliminary Report on Patentability and Written Opinion of PCT/KR2004/001197 dated Nov. 25, 2005, 5 pages.

European Search Report of EP 04734426.2 dated Feb. 4, 2011, 4 pages.

Bumm, L. A. et al., "Are Single Molecular Wires Conducting?," Science, American Association for the Advancement of Science, vol. 271, No. 5256, Mar. 22, 1996, pp. 1705-1707, XP000990723.

Kanayama, N. et al., "Interfacial Recognition of Sugars by Boronic Acid-Carrying Self-Assembled Monolayer", Langmuir, American Chemical Society, vol. 16, No. 2, Jan. 25, 2000, pp. 577-583, XP002997117.

* cited by examiner

BIOSENSOR FOR ANALYZING QUANTITATIVELY ANALYTE WITH A PREDETERMINED SIZE AND LARGER THAN, AND MANUFACTURING METHOD THEREOF

CROSS-REFERENCE TO RELATED APPLICATIONS

This application is a divisional of U.S. patent application Ser. No. 10/558,222 filed Sep. 18, 2006, which application is based on International Application No. PCT/KR2004/001197 filed May 21, 2004, which claims priority of Korean Patent Application No. 10-2003-0033068 filed May 23, 2003, the disclosures of which are incorporated herein by reference in their entireties.

TECHNICAL FIELD

The present invention relates generally to a biosensor for quantitatively analyzing a material having a certain predetermined or larger size and a manufacturing method thereof. The present invention relates particularly to a nanometer scale structure having an exposed conductive region of a certain diameter distributed on an insulated metallic substrate in a desired pattern or randomly, and a method of quantitatively analyzing a bio-material using the nanometer scale structure.

BACKGROUND ART

Conventionally, an exposed conductive region having a micrometer scale or larger area can be formed on an insulated metallic substrate by means of a variety of techniques pertaining to the well-known semiconductor process. Due to the limitations of conventional techniques, however, a formation of exposed conductive regions of a nanometer scale faces a number of obstacles. Various approaches have been attempted to overcome these obstacles. See, for example, U.S. Pat. Nos. 6,503,701, 6,492,096, 6,322,963, 6,001,587, and 5,922,2146.

On the other hand, a monolayer of self-assembled molecular (hereinafter, referred to a "monolayer SAM") may be described by a state in which an organic compound containing thiols (—SH) or disulfides (—S—S) is aligned in the form of a mono-layer by covalent-bonding of the sulfuric functional group of the compound with a metallic electrode made of gold or platinum or the like. For example, the monolayer SAM may be formed by steps of preparing an aqueous solution of the self-assembling material dissolved in a solvent such as water or various organic solvent, contacting the solution with a metallic substrate (immersion in the solution or dropping of the solution on the substrate) and reacting for a certain period of time, and rinsing out the un-reacted reagents. These monolayer SAMs may be employed to modify a metallic surface, i.e., its hydrophobic surface to a hydrophilic, and vice versa. They also may serve as a linker for a bio-material to be bound to a metallic material. Although a number of patents have attempted to apply the SAM techniques to the fabrication of biosensors, it is found out that a commercialized biosensor using the SAM technique has not been reported yet.

The reported conventional techniques pertaining to the monolayer SAM are related mostly to methods of forming a monolayer SAM on a conductive metallic material such as gold or platinum or the like, techniques for fixing a bio-material, such as protein and DNA, to the functional groups in the end of the created SAM, and characterization of materials to be fixed to the SAM monolayer. Those techniques are disclosed, for example, in U.S. Pat. Nos. 4,964,972, 5,652,059, 5,686,549, 5,725,788, 5,827,417, 5,922,214, 6,031,756, 6,114,099, 6,127,127, 6,156,393, 6,183,815, 6,270,946, 6,287,874, 6,312,809, 6,322,979, 6,346,387, 6,432,723, 6,436,699, 6,444,318, 6,444,321, 6,492,096, and 6,114,099.

The quantitative analysis of protein has been carried out through the application of immuno-reaction, a typical one of which is the enzyme-linked immuno Sorbent Assay (ELISA). In ELISA, a primary antibody, which is specifically fixed to the protein to be analyzed, is fixed to a substrate. Thereafter, a secondary antibody bondable to the primary antibody is bound thereto. A label substance is attached to the secondary antibody and the label substance has fluorescence or radioactivity. Therefore, the concentration of the protein can be quantitatively analyzed by measuring the intensity of the signal resulting from the fluorescence or radioactivity.

It has been found out that the above conventional techniques have several problems. Typically, it requires a rinsing and cleaning procedure in order to remove non-specifically bonded enzyme or antibody, and needs separate equipment for detecting the fluorescence or radioactivity from the label substance. Those disadvantages lead to a large scale of the whole measurement outfit, a longer period of time for analyzing (for example, several hours), and an increase in the cost of equipment (for example, several tens of thousand dollars). There is therefore a limitation in commercializing a portable analyzer that can be used by small-sized hospitals or non-professional individuals.

DISCLOSURE OF THE INVENTION

It is an object of the invention to provide a universal analyzer interface which can analyze a variety of bio-molecules, and a method of quantitatively analyzing the bio-molecules using the interface.

A further object of the invention is to provide a system for electrochemically analyzing the bio-materials, which leads to the production of a portable, and miniaturized analyzer.

A further object of the invention is to overcome the disadvantages and problems in the prior art, i.e., to remove the rinsing or cleaning step, thereby reducing the time for analyzing, and enhancing the convenience of operation.

According to one aspect of the invention, there is provided a biosensor for quantitatively analyzing a predetermined and larger sized material. The biosensor comprises an electrode substrate, a plurality of first monolayer molecules formed on the electrode substrate wherein the first monolayer molecules has a diameter less than that of the material to be analyzed and has electrochemical conductivity, and a second monolayer molecules formed on the electrode substrate except for the region where the first monolayer molecules are formed wherein the second monolayer molecules has electrochemical dielectricity. The first monolayer molecules forms an exposed conductive region, and the second monolayer molecules forms an insulated region. The biosensor further comprises a signal medium having a size capable of diffusing through the exposed conductive region formed the first monolayer molecules, wherein the signal medium is formed of a first material which can be bound specifically to the material to be analyzed and a second material which can produce an electro-chemical signal.

Preferably, the exposed conductive region formed by the first monolayer molecules has a constant diameter or area. Also, the exposed conductive region formed by the first monolayer molecules comprises a self-assembled monolayer molecules having a nano-scale diameter. Herein, the nano-scale denotes the order of 0.1 to 10 nanometers. The first monolayer molecules is formed of an organic compound containing thiols or disulfides, preferably, formed of one selected from the group consisting of 3-mercatopropionic acid, cysteamine, and cystamine. The second monolayer molecules also comprises a self-assembled monolayer molecules and is formed of a 1-decanethiol series compound. The electrode substrate may be formed of gold or platinum.

According to another aspect of the invention, there is provided a method of manufacturing a biosensor for quantitatively analyzing a predetermined and larger sized material. The method comprises steps of forming a first self-assembled monolayer molecules on an electrode substrate wherein the self-assembled monolayer molecules has a functional group bound to the end of a portion of molecules thereof such that the functional group can be bound specifically to a giant molecule which determines the size of the material to be analyzed by the biosensor, providing the giant molecule and binding the giant molecule with the functional group, substituting with a second self-assembled monolayer molecules the first self-assembled monolayer molecules except for the regions blocked by the giant molecule wherein the second self-assembled monolayer molecules has electrochemical dielectricity, and removing the giant molecule.

According to the present invention, the quantitative analysis of protein can be carried out by means of simplified procedures, without the necessity of rinsing out a signal-producing material, which is non-specifically bonded to the materials to be analyzed. The present invention provides a universal analyzer using only the size of the molecules and thus there is no limitation in the kind of materials to be analyzed. A selective and separate analysis can be realized in which interference caused by other materials is significantly reduced.

BRIEF DESCRIPTION OF DRAWINGS

Further objects and advantages of the invention can be more fully understood from the following detailed description taken in conjunction with the accompanying drawings in which.

BEST MODE FOR CARRYING OUT THE INVENTION

Figure 1A:
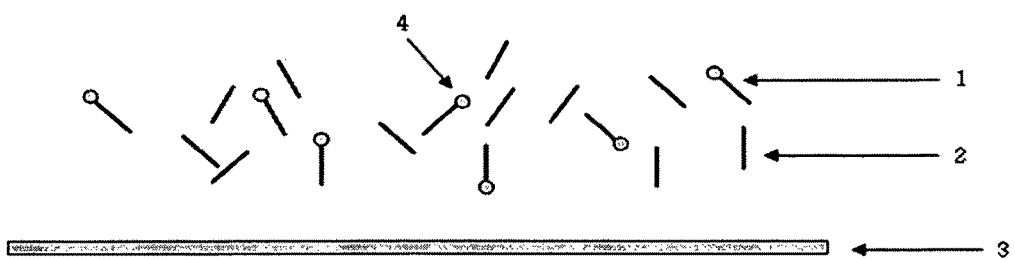
FIG. 1 illustrates the steps of forming a hybrid self-assembled monolayer molecules according to one embodiment of the invention.

Referring to the accompanying drawings, the embodiments according to the present invention are described in detail hereafter. The same reference numerals are used in different FIGures to denote similar or identical components.

Figure 1B:
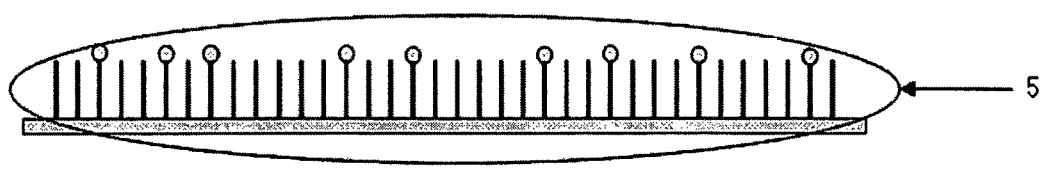

FIG. 1 illustrates steps of forming a hybrid self-assembled monolayer molecules according to one embodiment of the invention. In this description, the self-assembled monolayer molecules will be referred to as a "monolayer SAM" or a "SAM monolayer." The SAM monolayer is formed of a hybridization of a first thiol molecule 1 and a second thiol molecule 2. The first thiol molecule 1 has a material covalently bonded thereto that is able to bind to a protein molecule of a certain size, which determines the area of an exposed conductive region. The second thiol molecule 2 has a short carbon-chain such that it can prevent a non-specific adsorption of protein, simultaneously while maintaining sufficient electrochemical conductivity. As shown in FIG. 1a, a solution containing the chemically-distinct self-assembling molecules is prepared and a metallic substrate 3 (also, referred to as "electrode substrate") is immersed in the solution. Alternatively, the solution may be dropped on the metallic substrate 3. After a certain period of time, as shown in FIG. 1b, the sulfur atom of the thiol molecules is covalently bound to, for example, gold atoms of the metallic substrate 3, thereby forming the hybrid SAM monolayer 5.

Although a number of materials may be used for the metallic substrate 3 so long as they can form a SAM monolayer thereon, gold or platinum is preferable for the electrochemical biosensor interface of the invention since they have good electrochemical characteristics. Gold is more preferable because of its relatively low cost, simple treatment procedures, favorable adhesion with plastic materials, and high conductivity.

According to the invention, most organic compounds containing thiols (—SH) or disulfides (—S—S) may be utilized as molecules forming the hybrid SAM. It is preferable that the length of carbon-chain in the compounds is short so that they can carry out electrochemical oxidation and reduction reactions. By way of examples, the materials having the above properties include 3-mercatopropionic acid, cysteamine, cystaminem and the like, particularly, cysteamine, or cystamine is preferable since the length of their carbon-chain is composed of two carbon atoms.

The first thiol molecule 1 has a material covalently bonded thereto, which can be specifically bondable to a giant molecule of a certain size and determine the area of exposed conductive region that is one of the features of the invention. According to one embodiment of the invention, the first thiol molecule 1 may be formed by artificially covalent-bonding the second thiol molecule 2 to a molecule 4 (hereinafter, also referred to as a "functional group" or "desthio-biotin") which is capable of binding specifically to the giant molecule having a certain size. It is preferable that a commercial product or preformed molecule 4, after purification, is mixed with the second thiol molecules 2 to produce the first thiol molecule 1 as described above. The giant molecule to be used for determining the area of exposed region and the material 4 to be bondable specifically thereto may be selected from a number of bonding pairs so long as the selected pair of materials can be reversibly bound. For example, the reversible bonding pair includes enzyme-antibody, avidin-biotin, or the like. Any bonding pair, which can be controlled by means of electrostatic force or affinity of materials, may be employed. Particularly, the avidin-biotin pair, among others, has a strong bonding force and also can be led to a reversible bonding. Therefore, the case of avidin-biotin bonding pair will be illustrated below, referring to FIG. 2.

Figure 2A:
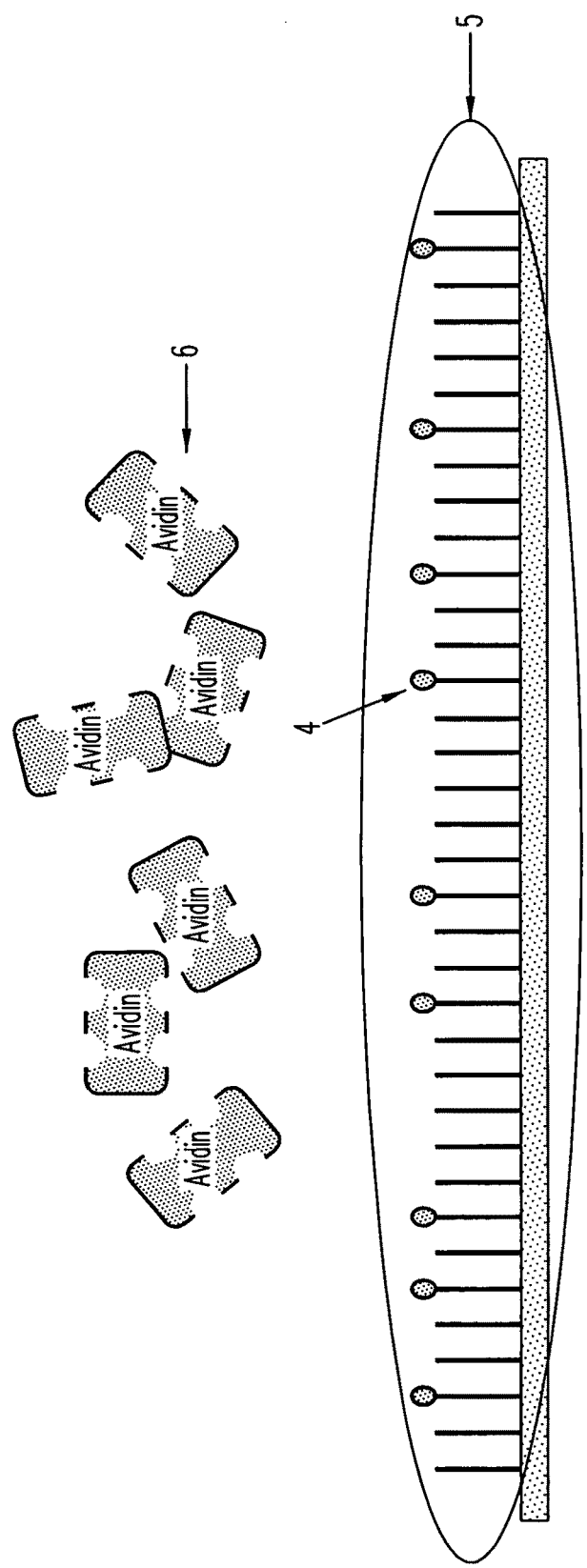
FIG. 2 illustrates the steps of binding avidin with desthio-biotin in order to determine the area of exposed conductive regions according to one embodiment of the invention.

FIG. 2 shows steps of binding avidin with desthio-biotin in order to determine the area of exposed conductive regions according to one embodiment of the invention. As shown in FIG. 2a, a giant molecule 6 introduced into the electrode substrate 5 of FIG. 1b is bonded to the specific functional group 4 present in the surface of the SAM monolayer 5. The giant molecule 6 may be introduced simply in a form of solution and kept for a period of time at room temperature until the bonding process is completed. As described above, enzyme-antibody, avidin-biotin, or the like may be employed as the materials 4 and 6. This embodiment will be described with reference to the avidin-biotin bonding pair, which can be reversibly bonded.

Figure 2B:
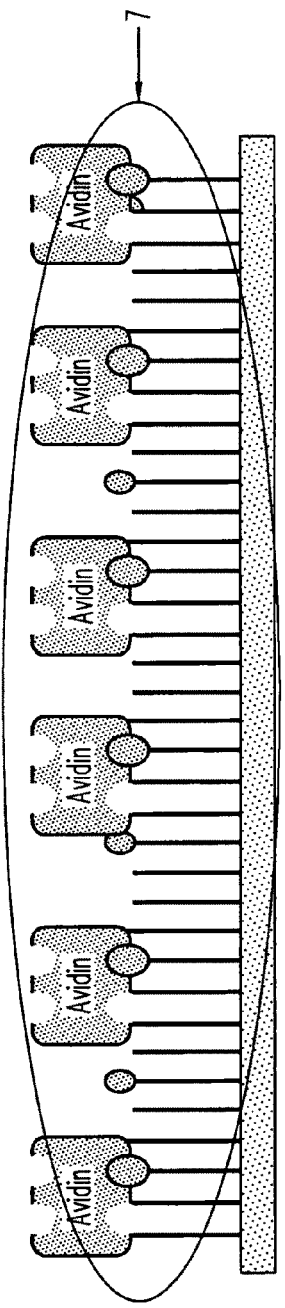

The avidin is a kind of proteins having four bonding sites and can be bound specifically to biotin with a strong bonding force. However, since the control of reversible bonding is one of required properties, when biotin is employed as the specific functional group 4, it is not easy to reversibly control their bonding. Therefore, in this case, desthio-biotin having a less strong bonding force is preferred. Desthio-biotin is a molecule where a sulfur atom is removed from biotin, and thus the particular bonding with avidin is identical to that of biotin, but its bonding force is a bit weaker than biotin. Therefore, their bonding can be reversibly controlled through a competitive reaction, which utilizes the difference of bonding force between biotin and desthio-biotin. According to those procedures describe above, a hybrid interface 7 formed of SAM monolayer and giant molecule is produced as shown in FIG. 2b. The hybris interface 7 is substituted as is explained below, referring to FIG. 3.

Figure 3A:
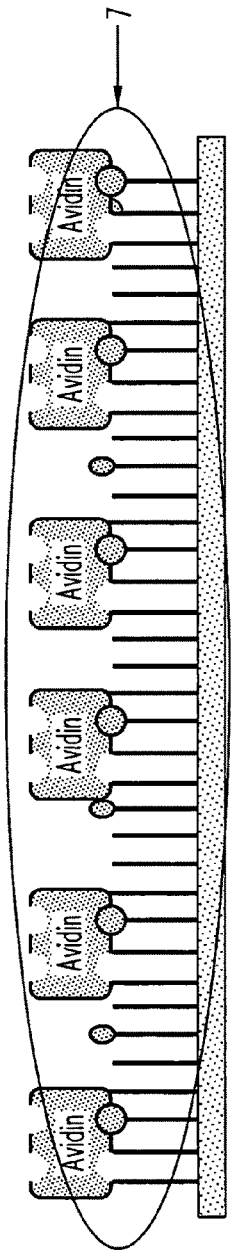
FIG. 3 shows the steps of forming an insulated region by substituting the self-assembled monolayer molecules according to one embodiment of the invention.
Figure 3B:
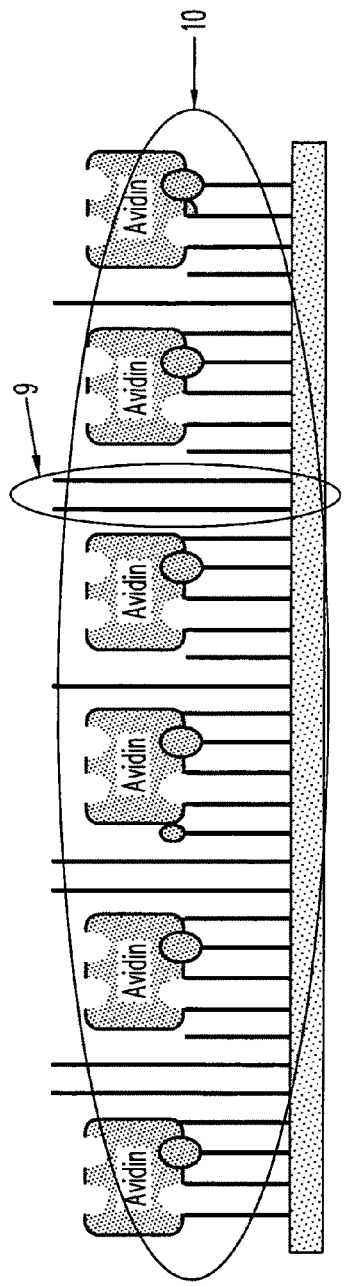

FIG. 3 depicts the steps of forming an insulated region by substituting the SAM monolayer according to one embodiment of the invention. The insulated region 9 works to insulate the area except for the exposed conductive region blocked as described in connection with FIG. 2, thereby being able to selectively detecting signals, depending on the size of the materials to be analyzed. The process shown in FIG. 3 may be carried out by means of substitution reaction. As previously describe, the substitution reaction may occur by dropping a solution of a desired molecule and maintaining for a period of time until the reaction is completed. In the substitution reaction, a new self-assembling molecule 8 substitutes molecules present in the region other than the blocked region by the giant molecules in the hybrid interface 7. On completion of the reaction, the un-reacted molecules and substituted molecules are rinsed out. Preferred materials for use as the dielectric self-assembling molecule 8 are molecules having a sufficient length of carbon-chain to prevent the electric current flow. 1-decanethiol series compounds are more preferred, which have a long carbon-chain corresponding to ten carbon atoms. Consequently, an intermediate interface 10 is formed according to the procedures as shown in FIG. 3. From the intermediate interface 10, the giant molecule 6 is removed as explained below, referring to FIG. 4.

Figure 4A:
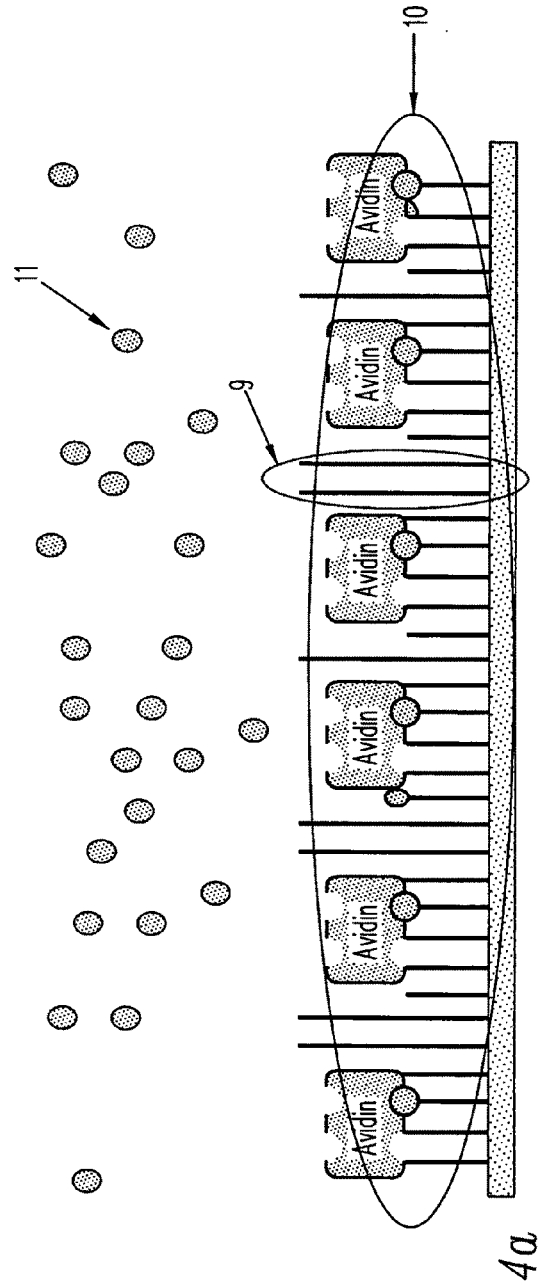
FIG. 4 illustrates the steps of removing avidin by applying biotin according to one embodiment of the invention.

FIG. 4 illustrates a step of removing avidin by applying biotin according to one embodiment of the invention. The intermediate interface 10 shown in FIG. 3 is completely insulated without any exposed conductive regions allowing for current flow. An exposed conductive region is, therefore, inevitably required in order to embody an electrochemical biosensor interface. For the purpose of forming an exposed conductive region, a competitive reaction may be employed. That is, the avidin 6 (the giant molecule) can be separated from the intermediate interface 10 by competitively reacting the desthio-biotin 4 bound to the avidin 6 with biotin 11, such that an exposed conductive region can be formed in the site where the avidin has been removed.

Figure 4B:
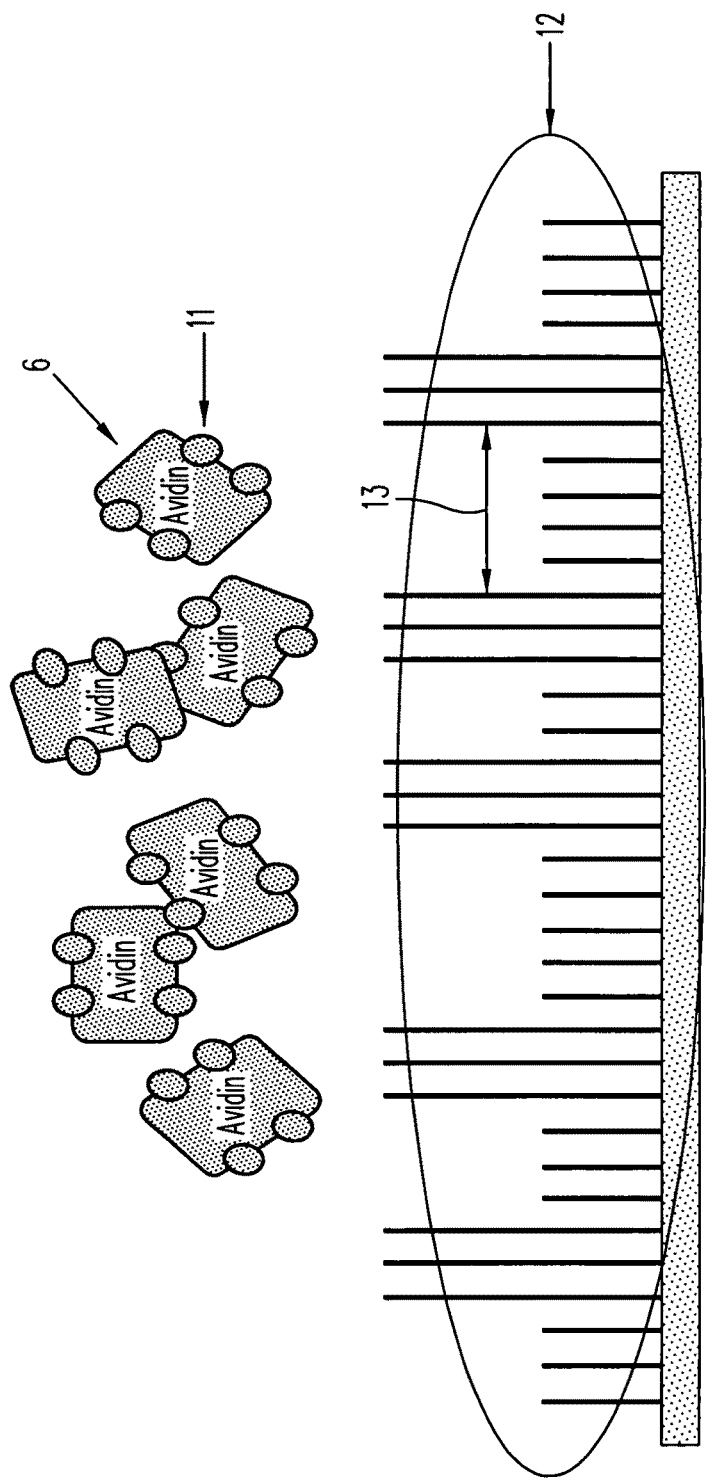

Similarly, the competitive reaction may be carried out by contacting the biotin solution 11 with the intermediate interface 10 and waiting for a certain period of time. When the biotin solution 11 is contacted with the intermediate interface 10, the avidin 6 is removed from the intermediate interface 10 due to a stronger bonding force of between the biotin 11 and the avidin 6 than between the avidin 6 and desthio-biotin 4. Consequently, a hybrid SAM interface 12 is formed as shown in FIG. 4b. The hybrid SAM interface 12 comprises an exposed conductive region 13, which is a significant feature of the invention. The width of the exposed conductive region 13 is determined by the giant molecule 6 such as avidin, which is illustrative of the invention.

FIG. 5 illustrates the procedures and principles for quantitatively analyzing glycated hemoglobin (HbA1c) using the biosensor of the invention. For the application of the hybrid SAM interface 12 to quantitative analysis of materials, two additional materials are required, along with the interface. One of them is a material 15 (also, referred to as a "binding material") capable of binding specifically to the material to be analyzed. The other one is a material 16 (also, referred to as a "signal or electron-transferring material") being able to produce electrochemical or optical signals. By way of example, analysis of HbA1c 17 will be described below, for an illustration of the present invention.

The HbA1c 17 is known to bind to the derivatives of boric acid (as the binding material 15). However, the known boric acid derivatives are incapable of producing a signal for the convenient use in the present invention. Therefore, an electron-transferring medium 16 is synthesized to the boric acid derivative 15 in order to pre-form a boric acid compound 14 (also, referred to as a "hybrid signal medium"), which can produce an electrochemical signal for convenient use in the invention. The synthesis procedures are well known to those skilled in the art and will not be explained herein. For the use in the present invention, the hybrid signal medium 14 requires several characteristics. For example, the hybrid signal medium 14 must have a small size enough to readily diffuse into the exposed conductive region, be capable of effectively binding effectively to the materials to be analyzed, and be able to intermediate between electrochemical oxidation and reduction reactions.

Figure 5A:
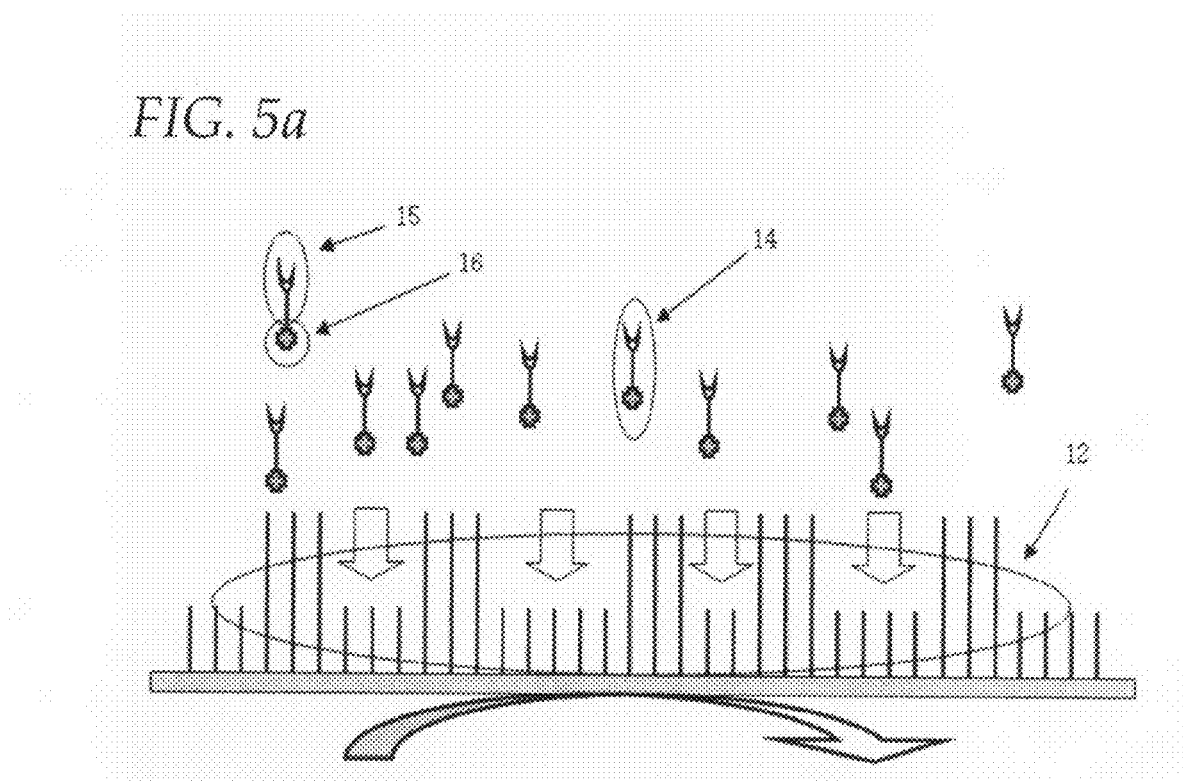
FIG. 5 shows the procedures and principles for quantitatively analyzing glycated hemoglobin (HbAlc) using the biosensor of the invention.

FIG. 5a shows the hybrid SAM interface 12 of the invention without any materials to be analyzed. As describe above, the hybrid signal medium 14 has a small size enough that it can diffuse into the exposed conductive region 13 of the interface 12 and transfer the electrons into and from the electrode substrate 3 such as a gold substrate. Therefore, when the material to be analyzed is not present on the interface 12, the intensity of the signal produced will be higher, compared to a state where the material is present in the interface 12.

Figure 5B:
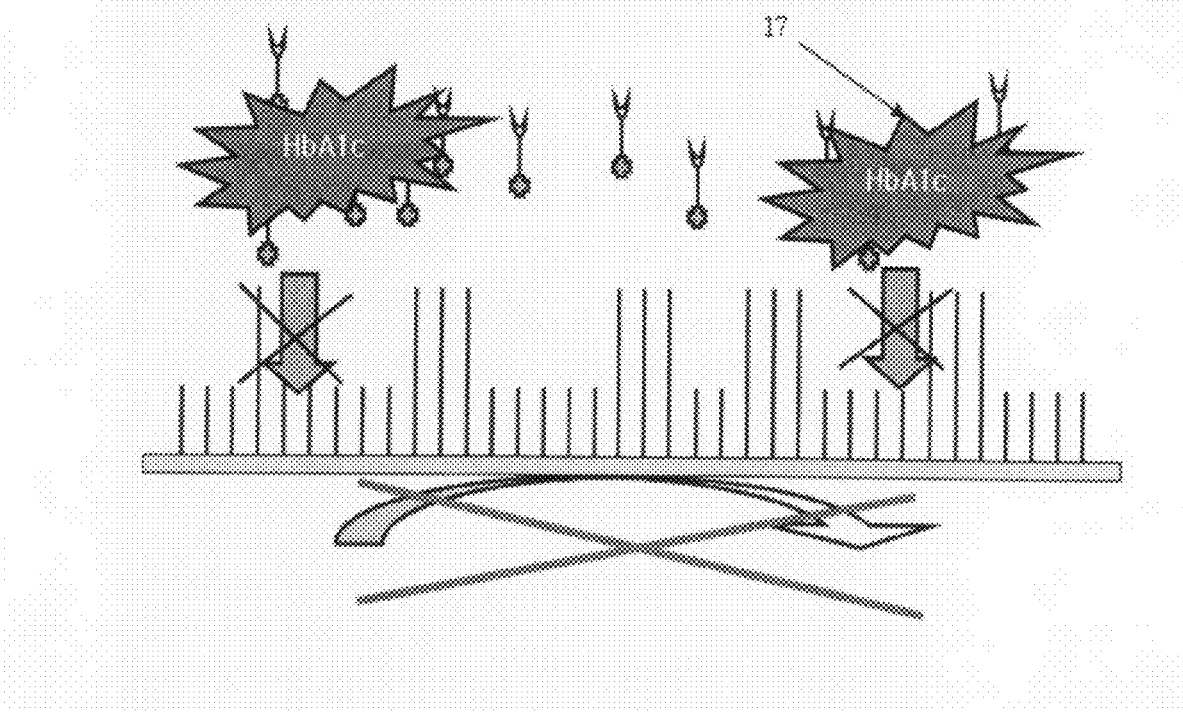

FIG. 5b illustrate the hybrid SAM interface 12 where the material to be analyzed such as HbA1c 17 is present. In this case, the binding material 15 of the hybrid signal medium 14 is made to bind to the HbA1c 17 such that the signal medium 14 can not diffuse as freely as in a state of single molecule. Simultaneously, since the HbA1c 17 to be analyzed has a size larger than that of the exposed conductive region 13, it can not reach the electrode substrate 3, thereby being unable to transfer electron therebetween. Consequently, when the material to be analyzed is present on the interface 12, the intensity of the signal produced will be lower, compared to a state where the material in the interface 12. Therefore, quantitative analysis of materials can be realized by using the hybrid SAM interface 12 and the analyzing principles according to the present invention.

Industrial Applicability

As described above, according to the present invention, the quantitative analysis of protein can be carried out by means of simplified procedures, without the necessity of rinsing out a signal-producing material which is non-specifically bonded to the materials to be analyzed. The present invention provides a universal analyzer using only the size of the molecules and thus there is no limitation in the kind of materials to be analyzed. A selective and separate analysis can be realized in which interference caused by other materials is significantly reduced.

While the present invention has been described with reference to the particular illustrative embodiments, it is not to be restricted by the embodiments but only by the appended claims. It is to be appreciated that those skilled in the art can change or modify the embodiments without departing from the scope and spirit of the present invention.

What is claimed is:

1. A biosensor for quantitatively analyzing a material having a predetermined and larger size, the biosensor comprising:
    a) an electrode substrate;
    b) a plurality of first monolayer molecules having electrochemical conductivity and forming an exposed conductive region on the electrode substrate, the exposed conductive region having a diameter less than that of the material to be analyzed; and
    c) a plurality of second monolayer molecules formed on the electrode substrate excluding the area where the first monolayer molecules are formed, the second monolayer molecules having electrochemical dielectricity.

2. A biosensor according to claim 1, wherein the second monolayer molecules forms an insulated region.

3. A biosensor according to claim 1, wherein the exposed conductive region from the first monolayer molecules has a constant diameter or area.

4. A biosensor according to claim 1, wherein the exposed conductive region formed by the first monolayer molecules has a nano-scale diameter.

5. A biosensor according to claim 1, further comprising signal medium formed of a first material which can be bound specifically to the material to be analyzed and a second material which can produce an electro-chemical signal, the signal medium being able to diffuse through the exposed conductive region formed by the first monolayer molecules.

6. A biosensor according to claim 1, wherein the first and second monolayer molecules include a self-assembled monolayer molecules.

7. A biosensor according to claim 6, wherein the first monolayer molecules is formed of an organic compound containing thiols or disulfides.

8. A biosensor according to claim 6, the second monolayer molecules is formed of an organic compound containing thiols or disulfides, 9. A biosensor according to claim 7, wherein the first monolayer molecules is formed of a compound which is able to form a self-assembled monolayer molecules having a length that enables electrochemical current flow.

10. A biosensor according to claim 9, wherein the first monolayer molecules is formed of any one selected from the group consisting of 3-mercatopropionic acid, cysteamine, and cystamine.

11. A biosensor according to claim 1, wherein the second monolayer molecules is formed of a compound which is able to form a self-assembled monolayer molecules having a length that enables electrochemical insulation.

12. A biosensor according to claim 11, wherein the second monolayer molecules is formed of a 1-decanethiol series compound.

13. A biosensor according to claim 1, wherein the electrode substrate is formed of gold or platinum.

* * * * *